US006753172B1

(12) United States Patent
Payne et al.

(10) Patent No.: US 6,753,172 B1
(45) Date of Patent: Jun. 22, 2004

(54) FABI

(75) Inventors: David John Payne, Phoenixville, PA (US); Peter Henry Milner, Great Dunmow (GB); Stewart Campbell Pearson, Berwyn, PA (US); John Timothy Lonsdale, Exton, PA (US)

(73) Assignee: Affinium Pharmaceuticals, Inc., Toronto (CA)

( * ) Notice: Subject to any disclaimer, the term of this patent is extended or adjusted under 35 U.S.C. 154(b) by 386 days.

(21) Appl. No.: 09/292,411

(22) Filed: Apr. 15, 1999

Related U.S. Application Data

(62) Division of application No. 08/790,043, filed on Jan. 28, 1997.
(60) Provisional application No. 60/024,845, filed on Aug. 28, 1996.

(51) Int. Cl.$^7$ .............................. C12N 9/00; C07K 1/00; C07K 14/00; C07K 16/00
(52) U.S. Cl. ....................... 435/183; 530/300; 530/324; 530/350
(58) Field of Search .......................... 435/183; 530/300, 530/324, 350; 424/190.1, 192.1, 234.1, 243.1

(56) References Cited

U.S. PATENT DOCUMENTS

| | | | |
|---|---|---|---|
| 5,539,132 A | 7/1996 | Royer et al. |
| 5,614,551 A | 3/1997 | Dick et al. |
| 5,759,837 A | 6/1998 | Kuhajda et al. |
| 5,965,402 A | 10/1999 | Black et al. |
| 6,228,619 B1 | 5/2001 | Foster et al. |
| 6,274,376 B1 | 8/2001 | Black et al. |
| 6,380,370 B1 | 4/2002 | Doucette-Stamm et al. |
| 6,403,337 B1 * | 6/2002 | Bailey et al. |
| 6,432,670 B1 | 8/2002 | Payne et al. |
| 6,593,114 B1 | 7/2003 | Kunsch et al. |
| 2002/0076766 A1 | 6/2002 | Black et al. |

FOREIGN PATENT DOCUMENTS

| | | |
|---|---|---|
| DE | 26 20 777 | 12/1977 |
| DE | 26 20 777 A1 | 12/1977 |
| EP | 0 78 6519 A2 | 7/1997 |
| EP | 0 826 774 A2 | 4/1998 |
| JP | 10-174590 | 6/1998 |
| WO | WO 97/30070 | 8/1997 |
| WO | WO 97/30149 | 8/1997 |
| WO | WO 00/70017 | 11/2000 |
| WO | WO 01/30988 | 5/2001 |
| WO | WO 01/48248 | 7/2001 |
| WO | WO 02/31128 | 4/2002 |

OTHER PUBLICATIONS

Bergler et al., "Protein EnvM is the NADH–dependent Enoyl–ACP Reductase (FabI) of *Escherichia coli*", The Journal of Biological Chemistry, vol. 269, No. 8, pp 5493–5496 (1994).

Bergler et al., "Sequences of the envM gene and of two mutated alleles in *Escherichia coli*", Journal of General Microbiology (1992), 138, pp. 2093–2100.

Broadwater et al., "Spinach Holo–Acyl Carrier Protein: Overproduction and Phosphopantetheinylation in *Escherichia coli* BL21 (DE3), In Vitro Acylation, and Enzymatic Desaturation of Histidine–Tagged Isoform $I_1$", Protein Expression and Purification 15, 314–326 (1999).

Edwards, et al., "Cloning of the fabF gene in an expression vector and in vitro characterization of recombinant fabF and fabB encoded enzymes from *Escherichia coli*", FEBS Letters, 402:62–66 (1997).

Grassberger et al., "Preparation and Antibacterial Activates of New 1,2,3–Diazaborine Derivatives and Analogues", Journal of Medicinal Chemistry, 1984, vol. 24, No. 8, pp. 947–953.

Gronowitz et al., "Antibacterial borazaro derivatives", Acta Pharm. Suecica 8, pp. 377–390 (1971).

Heath et al., "Enoyl–Acyl Carrier Protein Reductase (fabI) Plays a Determinant Role in Completing Cycles of Fatty Acid Elongation in *Escherichia coli*\*", The Journal of Biological Chemistry, vol. 270, No. 44, pp. 26538–26542 (1995).

Heath et al., "Regulation of Fatty Acid Elongation and Initiation by Acyl–Acyl Carrier Protein in *Escherichia coli*\*", The Journal of Biological Chemistry, vol. 271, No. 4, pp 1833–1836 (1996).

Lam et al., "Effect of diazaborine derivative (Sa 84.474) on the virulence of *Escherichia coli*", Journal of Antimicrobial Chemotherapy (1987) 20, pp. 37–45.

Lambalot, et al., "Cloning Over production, and Characterization of the *Escherichia coli* Holo–acyl Carrier Protein Synthase\*", The Journal of Biological Chemistry, vol. 270, No. 42, pp. 24658–24661 (1995).

Ngo et al., "Computational complexity, protein structure prediction and the Levinthal paradox", Chapter 14 in 'The Protein Folding Problem and Tertiary Structure Prediction', Merz et al. (eds.), Birkhauser: Boston, MA, pp. 433 & 492–495.

(List continued on next page.)

Primary Examiner—Mark Navarro
(74) Attorney, Agent, or Firm—Foley Hoag, LLP

(57) ABSTRACT

Prokayrotic FABI polypeptides and DNA (RNA) encoding such FABI and a procedure for such polypeptides by recombinant techniques is disclosed. Also disclosed are methods for utilizing such FABI for the treatment of infection, such as bacterial infections. Antagonists against such FABI and their use as a therapeutic to treat infections, such asstaphylococcal infections are also disclosed. Also disclosed are diagnostic assays for detecting diseases related to the presence of FABI nucleic acid sequences and the polypeptides in a host. Also disclosed are diagnostic assays for detecting polynucleotides encoding FABI and for detecting the polypeptide in a host.

13 Claims, 3 Drawing Sheets

OTHER PUBLICATIONS

Rock et al., "Preparative Enzymatic Synthesis and Hydrophobic Chromatography of Acyl–Acyl Carrier Protein", *The Journal of Biological Chemistry*, 254(15):7123–7128 (1979).

Rock et al., "Acyl Carrier Protein from *Escherichia coli*", *Methods in Enzymology*, 71:341–351 (1981).

Roujeinkova et al., "Inhibitor Binding System on Enoyl Reductase Reveal Conformational Changes Related to Substrate Recognition", *The Journal of Biological Chemistry*, 274(43): 30811–30817 (1999).

Turnowsky et al., "envM genes of Salmonella typhimurium and *Escherichia coli*", Journal of Bacteriology, Dec. 1989, pp. 6555–6565.

Ward et al., "Kinetic and Structural Characteristics of the Inhibition of Enoyl (Acyl Carrier Protein) Reductase by Triclosan", Biochemistry, 38: 12514–12525 (1999).

Turnowsky, et al., (1989), *J. Bacteriol., 171*: 6555–6565.

Bergler, et al., (1994), *J. Biol. Chem., 269*: pp 5493–5496.

Heath, et al., (1996), *J. Biol. Chem., 271*: 1833–1836.

Heath, et al., (1995), *J. Biol. Chem., 270*: 26538–26542.

Grassberger, et al., (1984), *J. Med. Chem., 27*: 947–953.

Gronowitz, et al., *Acta Pharma Suecica*, (1971), 8:377.

Bergler, et al., (1992), *J. Gen. Microbiol., 138*:2093–2100.

Lam, et al., *J. Antimirob. Chemother.*, (1987), 20: 37–45.

Ngo, et al., Chapter 14 in '*The Protein Folding Problem and Tertiary Structure Prediction*', Merz, et al. (eds.), Birkhauser: Boston, MA, pp. 433 & 492–495.

* cited by examiner

[SEQ ID NO:2]

```
  1  MLNLENKTYV IMGIANKRSI AFGVAKVLDQ LGAKLVFTYR KERSRKELEK
 51  LLEQLNQPEA HLYQIDVQSD EEVINGFEQI GKDVGNIDGV YHSIAFANME
101  DLRGRFSETS REGFLLAQDI SSYSLTIVAH EAKKLMPEGG SIVATTYLGG
151  EFAVQNYNVM GVAKASLEAN VKYLALDLGP DNIRVNAISA GPIRTLSAKG
201  VGGFNTILKE IEERAPLKRN VDQVEVGKTA AYLLSDLSSG VTGENIHVDS
251  GFHAIK
```

FIG. 1

[SEQ ID NO:1]

```
  1  ATGTTAAATC TTGAAAACAA AACATATGTC ATCATGGGAA TCGCTAATAA
 51  GCGTAGTATT GCTTTTGGTG TCGCTAAAGT TTTAGATCAA TTAGGTGCTA
101  AATTAGTATT TACTTACCGT AAAGAACGTA GCCGTAAAGA GCTTGAAAAA
151  TTATTAGAAC AATTAAATCA ACCAGAAGCG CACTTATATC AAATTGATGT
201  TCAAAGCGAT GAAGAGGTTA TTAATGGTTT TGAGCAAATT GGTAAAGATG
251  TTGGCAATAT TGATGGTGTA TATCATTCAA TCGCCATTGC TAATATGGAA
301  GACTTACGCG GACGCTTTTC TGAAACTTCA CGTGAAGGCT TCTTGTTAGC
351  TCAAGACATT AGTTCTTACT CATTAACAAT TGTGGCTCAT GAAGCTAAAA
401  AATTAATGCC AGAAGGTGGT AGCATTGTTG CAACAACATA TTTAGGTGGC
451  GAATTCGCAG TTCAAAATTA TAATGTGATG GGTGTTGCTA AAGCGAGCTT
501  AGAAGCAAAT GTTAAATATT TAGCATTAGA CTTAGGTCCT GATAATATTC
```

FIG. 2

| | | | | |
|---|---|---|---|---|
| 551 | GCGTTAATGC | AATTTCAGCT | GGTCCAATCC | GTACATTAAG | TGCAAAAGGT |
| 601 | GTGGGTGGTT | TCAATACAAT | TCTTAAAGAA | ATCGAAGAGC | GTGCACCTTT |
| 651 | AAAACGTAAC | GTTGATCAAG | TAGAAGTAGG | TAAAACAGCG | GCTTACTTRT |
| 701 | TAAGTGACTT | ATCAAGTGGC | GTTACAGGTG | AAAATATTCA | TGTAGATAGC |
| 751 | GGATTCCACG | CAATTAAATA | A | | |

FIG. 2A

US 6,753,172 B1

FABI

This application is a divisional of U.S. application Ser. No. 08/790,043, filed Jan. 28, 1997 which claims benefit of U.S. Provisional Application No. 60/024845, filed Aug. 28, 1996.

This invention relates, in part, to newly identified polynucleotides and polypeptides; variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists. In particular, in these and in other regards, the invention relates to polynucleotides and polypeptides of staphylococcal FabI enoyl-ACP reductase hereinafter referred to as "FABI".

BACKGROUND OF THE INVENTION

Although the overall pathway of saturated fatty acid biosynthesis is similar in all organisms, the fatty acid synthase (FAS) systems vary considerably with respect to their structural organization. Thus in Type I FAS systems, found in vertebrates and yeasts, the necessary enzymes required for fatty acid synthesis are present on one or two polypeptide chains respectively. In contrast, in Type II systems found in most bacteria and plants, each step in the pathway is catalysed by a separate mono-functional enzyme. It would therefore appear that significant selectivity of inhibition of the bacterial and mammalian enzymes is possible.

FabI (previously designated EnvM) functions as an enoyl-acyl carrier protein (ACP) reductase (Bergler, et al, (1994), *J. Biol. Chem.* 269, 5493–5496) in the final step of the four reactions involved in each cycle of bacterial fatty acid biosynthesis.

The first step is catalysed by β-ketoacyl-ACP synthase, which condenses malonyl-ACP with acetyl-CoA (FabH, synthase III). In subsequent rounds malonyl-ACP is condensed with the growing-chain acyl-ACP (FabB and FabF, synthases I and II respectively).

The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP which is in turn converted to acyl-ACP by NADH-dependent enoyl-ACP reductase (FabI). Further rounds of this cycle, adding two carbon atoms per cycle, eventually lead to palmitoyl-ACP (16C) where upon the cycle is stopped largely due to feedback inhibition of FabI by palmitoyl-ACP (Heath, et al, (1996), *J. Biol. Chem.* 271, 1833–1836). FabI is therefore a major biosynthetic enzyme which is also a key regulatory point in the overall synthetic pathway.

Early data suggested that there were two enoyl-ACP reductases in *E. coli*, one NADPH dependent and the other NADH dependent. However, more recent work has found no evidence for the NADPH dependent enzyme and FabI is the only enoyl ACP reductase identified in *E. coli*. (Heath, et al, (1995), *J. Biol. Chem.* 270, 26538–26542; Bergler, et al, (1994), *J. Biol. Chem.* 269, 5493–5496).

It has been shown that diazaborine antibiotics inhibit fatty acid, phospholipid and lipopolysaccharide (LPS) biosynthesis and it has also been shown that the antibacterial target of these compounds is FabI. For example derivative 2b18 from Grassberger, et al (1984) *J. Med Chem* 27 947–953 has been shown to be a non-competitive inhibitor of FabI having a Ki=0.2 mM (Bergler, et al, (1994), *J. Biol. Chem.* 269, 5493–5496). The antibacterial activity of diazaborine derivatives against Gram-negatives and Gram positive organisms is well documented (Grassberger et al., J Med Chem. 1984 27, 947–953; Gronowitz et al., Acta Pharm Suecica, 1971 8 377; Wersch et al U.S. Pat. No. 2,533,918; Lam et al., J. Antimirob. Chemother. 1987 20 37–45).

Conditionally lethal FabI mutants have been constructed in *E. coli* and the FabI gene from *Salmonella typhimurium* complements this mutation. In addition, plasmids containing the FabI gene from diazaborine resistant *S. typhimurium* conferred diazaborine resistance in *E. coli* (Turnowsky, et al, (1989), *J. Bacteriol.*, 171, 6555–6565) confirming FabI as the antibacterial target of diazaborines.

Inhibition of FabI either by diazaborine or by raising the temperature in an FabI temperature sensitive mutant to non-permissive conditions is lethal, thus demonstrating that FabI is essential to the survival of the organism (Bergler, et al, (1994), *J. Biol. Chem.* 269, 5493–5496). Laboratory generated point mutations in the FabI gene lead to diazaborine resistant *E. coli*.

FabI is conserved in Gram negative organisms with 98% identity between *E. coli* and *S. typhimurium* FabI (Bergler, et al, (1992), *J. Gen. Microbiol.*, 138, 2093–2100) and 75% identity between these proteins and *H. influenzae* FabI. *Staphylococcus aureus* FABI of the invention shows 54% similarity to the mycobacterial protein, InhA, which is highly conserved throughout mycobacteria including *M. tuberculosis*. *E. coli* FabI was found to be 34% identical, 57% similar to *Brassica napus* (rape seed) enoyl-ACP reductase and *S. aureus* FABI of the present invention was also 34% identical, 57% similar. Moreover, FABI of the present invention was found to be 44% identical, 64% similar over 252 amino acids to *E. coli* FabI. FABI of the present invention is only 27% identical, 48% similar to a mammalian 2,4-dienoyl-coenzyme A reductase. This mammalian homolog differs from FABI in that it is involved in the β-oxidation of polyunsaturated enoyl-CoAs and utilizes NADPH as cofactor rather than NADH. Therefore, there is significant potential for selective inhibition of FABI. Since there are no marketed antibiotics targeted against fatty acid biosynthesis it is likely that inhibitors of FABI will not be susceptible to current antibiotic resistance mechanisms. Moreover, this is a potentially broad spectrum target.

There is an unmet need for developing new classes of antibiotic compounds. Clearly, there is also a need for factors, such as FABI that may be used to screen compounds for antibiotic activity, such as a simple high through-put assay for screening inhibitors of FAS. Such factors may also be used to determine their roles in pathogenesis of infection, dysfunction and disease. Identification and characterization of such factors, which can play a role in preventing, ameliorating or correcting infections, dysfunctions or diseases are critical steps in making important discoveries to improve human health.

SUMMARY OF THE INVENTION

Toward these ends, and others, it is an object of the present invention to provide polypeptides, inter alia, that have been identified as novel FABI by homology between the amino acid sequence set out in FIG. 1 [SEQ ID NO:2] and known amino acid sequences of other proteins such as *E. coli* FabI enoyl-ACP reductase and those afforementioned.

It is a further object of the invention, moreover, to provide polynucleotides that encode FABI, particularly polynucleotides that encode the polypeptide herein designated FABI.

In a particularly preferred embodiment of this aspect of the invention the polynucleotide comprises the region encoding FABI in the sequence set out in FIG. 1 [SEQ ID NO:2].

In another particularly preferred embodiment of the present invention there is a novel FABI protein from *S. aureus* WCUH 29 comprising the amino acid sequence of SEQ ID NO:2, or a fragment, analogue or derivative thereof.

In accordance with this aspect of the invention there is provided an isolated nucleic acid molecule encoding a mature polypeptide expressible by the *Staphylococcus aureus* WCUH 29 strain contained in NCIMB Deposit No. 40771.

In accordance with this aspect of the invention there are provided isolated nucleic acid molecules encoding FABI, particularly staphylococcal FABI, including mRNAs, cDNAs, genomic DNAs and, in further embodiments of this aspect of the invention, biologically. diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of FABI.

In accordance with this aspect of the invention there are provided novel polypeptides of staphylococcal origin referred to herein as FABI as well as biologically, diagnostically or therapeutically useful fragments, variants and derivatives thereof, variants and derivatives of the fragments, and analogs of the foregoing.

It also is an object of the invention to provide FABI polypeptides, particularly FABI polypeptides, that may be employed for therapeutic purposes, for example, to treat disease, including treatment by conferring host immunity against infections, such as staphlococcal infections including, but not limited to infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophalmitis, preseptal and orbital cellulitis, darcryocystitis), kidney and urinary tract (e.g. epidymitis, intrarenal and perinephric abscess, toxic shock syndrome), skin (e.g. impetigo, folliculitis, cutaneous abscesses, cellulitis, wound infection, bacterial myositis), and bone and joint (e g. septic arthritis, osteomyelitis).

In accordance with yet a further aspect of the present invention, there is provided the use of a polypeptide of the invention for therapeutic or prophylactic purposes, for example, as an antibacterial agent or a vaccine.

In accordance with another aspect of the present invention, there is provided the use of a polynucleotide of the invention for therapeutic or prophylactic purposes, in particular genetic immunization.

Among the particularly preferred embodiments of this aspect of the invention are variants of FABI polypeptide encoded by naturally occurring alleles of the FABI gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned FABI polypeptides comprising culturing host cells having expressibly incorporated therein an exogenously-derived FABI-encoding polynucleotide under conditions for expression of FABI in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with yet another aspect of the present invention, there are provided inhibitors to such polypeptides, useful as antibacterial agents. In particular, there are provided antibodies against such polypeptides.

In accordance with certain preferred embodiments of this aspect of the invention, there are provided products, compositions and methods, inter alia, for, among other things: assessing FABI expression in cells by detecting FABI polypeptides or FABI-encoding mRNA; to treat bacterial infections in vitro, ex vivo or in vivo by exposing cells to FABI polypeptides or polynucleotides as disclosed herein; assaying genetic variation and aberrations, such as defects, in FABI genes; and administering a FABI polypeptide or polynucleotide to an organism to raise an immunological response against bacteria, such as, for example a staphylococcus.

In accordance with certain preferred embodiments of this and other aspects of the invention there are probes that hybridize to FABI sequences.

In certain additional preferred embodiments of this aspect of the invention there are provided antibodies against FABI polypeptides. In certain particularly preferred embodiments in this regard, the antibodies are highly selective for FABI.

In accordance with another aspect of the present invention, there are provided FABI agonists. Among preferred agonists awe molecules that mimic FABI, that bind to FABI-binding molecules or binding molecules, and that elicit or augment FABI-induced responses. Also among preferred agonists are molecules that interact with FABI, or with other modulators of FABI activities, and thereby potentiate or augment an effect of FABI or more than one effect of FABI and are bacteriostatic or bacteriocidal.

In accordance with yet ether aspect of the present invention, there are provided FABI antagonists. Among preferred antagonists are those which mimic FABI so as to bind to FABI-binding molecules but not elicit a FABI-induced response or more than one FABI-induced response. Also among preferred antagonists are molecules that bind to or interact with FABI so as to inhibit an effect of FABI or more than one effect of FABI or which prevent expression of FABI. Further particularly preferred antagonists of FABI lower or abolish a FABI enzymatic activity or activities.

In a further aspect of the invention there are provided compositions comprising a FABI polynucleotide or a FABI polypeptide for administration to cells in vitro, to cells ex vivo and to cells in vivo, or to a multicellular organism. In certain particularly preferred embodiments of this aspect of the invention, the compositions comprise a FABI polynucleotide for expression of a FABI polypeptide in a host organism to raise an immunological response, preferably to raise immunity in such host against bacteria, preferably staphylocci or closely genetically related organisms.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawing depicts certain embodiments of the invention. It is illustrative only and does not limit the invention otherwise disclosed herein.

FIG. 1 [SEQ ID NO:2] shows the polypeptide of *Staphylococcus aureus* FABI deduced from the polynucleotide of FIG. 2 and 2A [SEQ ID NO:1].

FIG. 2 [SEQ ID NO:1] shows the polynucleotide sequence of *Staphylococcus aureus* FABI.

GLOSSARY

The following illustrative explanations are provided to facilitate understanding of certain terms used frequently herein, particularly in the Examples. The explanations are provided as a convenience and are not limitative of the invention.

BINDING MOLECULE, as used herein, refers to mole or ions which bind or interact specifically with FABI polypeptides or polynucleotides of the present invention including, for example enzyme substrates and substrate and co-factor mimetics, as well as classical receptors (which also may be referred to as "binding molecules" and "interaction molecules," respectively and as "FABI binding molecules" and "FABI interaction molecules"). Binding between polypeptides of the invention and such molecules, including binding or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes a polypeptide of the invention.

Binding molecules also may be non-naturally occurring, such as antibodies and antibody-derived reagents that bind specifically to polypeptides of the invention.

DIGESTION of DNA refers to cleavage of DNA with a restriction enzyme that acts only at certain sequence in the DNA. The various restriction enzymes referred to herein are commercially available and their reaction conditions, cofactors and other requirements for use are, well known and routine to the skilled artisan.

For analytical purposes, typically, 1 μg of plasmid or DNA fragment is digested with about 2 units of enzyme in about 20 μl of reaction buffer. For the purpose of isolating DNA fragments for plasmid construction, typically 5 to 50 μg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the suppliers instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed, transfected, infected, or entered by an exogenous polynucleotide sequence, or is capable of transformation, infection, transfection, or entry by an exogenous polynucleotide sequence.

IDENTITY or SIMILARITY, as known in the art, are relationships between two polypeptide sequence or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods commonly employed to determine identity or similarity between two sequences include, but are not limited to those disclosed in Carillo, H., and Lipman, D., SIAM *J. Applied Math.*, 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., (1984) *Nucleic Acids Research* 12(1): 387), BLASTP, BLASTN, and FASTA (Atschul, S. F. et al., (1990) *J. Molec. Biol.* 215: 403).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosone and cell in which it naturally occurs.

As part of or following isolation, such polynucleotides can be joined to other polynucleotides, such as DNAs, for mutagenesis, to form fusion protein, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., *MOLECULAR CLONING, A LABORATORY MANUAL*, 2nd Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides. Often the term refers to single-stranded deoxyribonucleotides, but it can refer as well to single- or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art.

Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art.

Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) globally refers to any polyribonucleotide or polydeoxribonucleotide, which may be unmodified RNA or DNA or modified RNA or DNA Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide, derivative, covalent attachment of a lipid or lipid derivative, covalent attachment of phosphotidylinositol cross-linking, cyclization, disulfide bond formation, demethylation, formation of covalent cross-links, formation of cystine, formation of pyroglutamate, formylation, gamma-carboxylation, glycosytation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS—STRUCTURE AND MOLECULAR PROPERTIES*, 2nd Ed., T. E. Creighton, W.H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS*, B. C. Johnson Ed., Academic Press, New York (1983); Seifter et al., (1990) *Meth. Enzymol.* 182:626–646 and Rattan et al., (1992) *Protein Synthesis: Posttranslational Modifications and Aging*, Ann. N.Y. Acad. Sci. 663: 48–42.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention.

The modifications that occur in a polypeptide often will be a function of how it is made. For polypeptides made by expressing a cloned gene in a host, for instance the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired a polypeptide should be expressed in a glycosylating host, generally a eukaryotic cell.

It will be appreciated that the same type of modification may be present in the same or varying degree at several sites in a given polypeptide. Also, a given polypeptide may contain many types of modifications.

In general as used herein, the term polypeptide encompasses all such modifications, particularly those that are present in polypeptides synthesized by expressing a polynucleotide in a host cell.

TRANSFORMATION is the process by which a cell is "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is often one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

VARIANT(S) of polynucleotides or polypeptides, as the term is used herein are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

DESCRIPTION OF THE INVENTION

The present invention relates to novel FABI polypeptides and polynucleotides, among other things, as described in greater detail below. In particular, the invention elates to polypeptides and polynucleotides of a novel FABI gene of *Staphylococcus aureus*, which is related by amino acid sequence homology to FabI enzymes from Mycobacteria (InhA). *H. influenzae, Brassica napus* (rape seed) enoyl-ACP reductase, and to the *E. coli* FabI protein.

The invention relates especially to FABI having the nucleotide and amino acid sequences set out in FIG. 2 [SEQ D NO:1] and FIG. 1 [SEQ ID NO:2] respectively, and to the FABI nucleotide sequences in NCIMB Deposit No. 40771 and amino acid sequences encoded therefrom, which is herein referred to as "the deposited clone" or as the "DNA of the deposited clone." It will be appreciated that the nucleotide and amino acid sequence set out in FIG. 1 [SEQ D NO:2] and FIG. 2 [SEQ ID NO:1] were obtained by sequencing the FABI DNA of the deposited clone. Hence the sequence of the deposited clone is controlling as to any discrepancies between it (and the sequence it encodes) and the sequences of FIG. 1 [SEQ ID NO:2] or FIG. 2 [SEQ ID NO:1].

Polynucleotides

In accordance with one aspect of the present invention, there are provided isolated polynucleotides which encode the FABI polypeptide having the deduced amino acid sequence of FIG. 1 [SEQ ID NO:2].

Using the information provided herein, such as the polynucleotide sequence set out in FIG. 2 [SEQ ID NO:1], a polynucleotide of the present invention encoding FABI polypeptide may be obtained using standard cloning and screening procedures, such as those for cloning genomic DNAs from bacteria using Staphylococcus aureus WCUH29 cells as starting material. Illustrative of the invention, the polynucleotide set out in FIG. 2 [SEQ ID NO:1] was discovered in a genomic DNA library derived from Staphylococcus aureus WCUH29.

FABI of the invention is structurally related to other protein of the enoyl-ACP reductase family, as shown by the results of sequencing the genomic DNA encoding FABI in the deposited clone. The DNA sequence thus obtained is set out in FIG. 2 [SEQ ID NO:1]. It contains an open reading frame encoding a protein of about 256 amino acid residues with a deduced molecular weight of about 27.99 kDa. The protein exhibits greatest homology to the E. coli FabI protein among known proteins. FABI of FIG. 1 [SEQ ID NO:2] has about 44% identity and about 64% similarity with the amino acid sequence of E. coli enoyl (ACP) reductase (FabI), SwissProt Acession Number P29132.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be doubler stranded or single-strand. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 2 [SEQ ID NO:1]. It also maybe a polynucleotide with a different sequence, which, as a result of the redundancy (degeneracy) of the genetic code, encodes the polypeptide of the DNA of FIG. 1 [SEQ ID NO:2].

Polynucleotides of the present invention which encode the polypeptide of FIG. 1 [SEQ ID NO:2] may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequences which encode additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexa-histidine as discussed, this should include other tagging approaches peptide, such as the tag provided in the pQE vector (Qiagen, Inc.), among others, many of which are commercially available. As described in Gentz et al., (1989) *Proc. Natl. Acad. Sci., USA* 86: 821–824, for instance, hexa-histidine provides for convenient purification of the fusion protein. The HA tag may also be used to create fusion proteins and corresponds to an epitope derived of influenza hemagglutinin protein, which has been described by Wilson et al., (1984) *Cell* 37: 767, for instance.

In accordance with the foregoing, the term "polynucleotide encoding a polypeptide" as used herein encompasses polynucleotides which include a sequence encoding a polypeptide of the present invention, particularly staphylococcal FABI having the amino acid sequence set out in FIG. 1 [SEQ ID NO:2]. The term encompasses polynucleotides that include a single continuous region or discontinuous regions encoding the polypeptide (for example, interrupted by integrated phage, insertion sequence, recombination, or editing) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 1 [SEQ ID NO:2]. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of FABI set out in FIG. 1 [SEQ ID NO:2]; variants, analogs, derivatives and fragments thereof, and fragments of the variants, analogs and derivatives.

Further particularly preferred in this regard are polynucleotides encoding FABI variants, analogs, derivatives and fragments, and variants, analogs and derivatives of the fragments, which have the amino acid sequence of FABI polypeptide of FIG. 1 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of FABI. Also especially preferred in this regard are conservative substitutions. Most highly preferred are polynucleotides encoding polypeptides having the amino acid sequence of FIG. 1 [SEQ ID NO:2], without substitutions.

Further preferred embodiments of the invention are polynucleotides that are at least 70% identical to a polynucleotide encoding FABI polypeptide having the amino acid sequence set out in FIG. 1 [SEQ ID NO:2], and polynucleotides which are complementary to such polynucleotides. Alternatively, most highly preferred are polynucleotides that comprises a region that is at least 80% identical to a polynucleotide encoding FABI polypeptide encoded by the *Staphylococcus aureus* DNA of the deposited clone and polynucleotides complementary thereto or as set out in FIG. 2 [SEQ ED NO:1]. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiment in this respect, moreover, are polynucleotides which encode polypeptides which retain substantially the same biological function or activity as the mature polypeptide encoded by the DNA of FIG. 2 [SEQ D NO:1].

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding FABI and to isolate cDNA and genomic clones of other genes that have a high sequence similarity to the FABI gene. Such probes generally will comprise at least 15 bases. Preferably, such probes will have at least 30 bases and may have at least 50 bases. Particularly preferred probes will have at least 30 bases and will have 50 bases or less.

For example, the coding region of the FABI gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine which members of the library the probe hybridizes to.

The polynucleotides and polypeptides of the present invention may be employed as research reagents and materials for discovery of treatments of and diagnostics for disease, particularly human disease, as further discussed herein relating to polynucleotide assays, inter alia.

The polynucleotides of the invention that are oligonucleotides, including SEQ ID NOS:3 and 4, derived from the sequence of SEQ ID NO:1 may be used as PCR primers in the processes herein described to determine whether or not the *Staphylococcus aureus* genes identified herein in whole or in part are transcribed in infected tissue. The invention also provides that such sequences may also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypetite.

Deposited Materials

A deposit containing a *Staphylococcus aureus* WCUH 29 strain has been deposited with the National Collections of Industrial and Marine Bacteria Ltd. (NCIMB), 23 St. Machar Drive, Aberdeen AB2 1RY, Scotland on 11 September 1995 and assigned NCIMB Deposit No. 40771. The FABI clone deposit is referred to herein as "the deposited clone" or as "the DNA of the deposited clone."

The deposited material is a strain that contains the full length FABI DNA, referred to as "NCIMB 40771" upon deposit.

The sequence of the polynucleotides contained in the deposited material, as well as the amino acid sequence of the polypeptide encoded thereby, are controlling in the event of any conflict with any description of sequences herein.

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

A license may be required to make, use or sell the deposited materials, and no such license is hereby granted.

Polypeptides

The present invention further relates to a prokaryotic FABI polypeptide which has the deduced amino acid sequence of FIG. 1 [SEQ ID NO:2].

The invention also relates to fragments, analogs and derivatives of these polypeptides. The terms "fragment," "derivative" and "analog" when referring to the polypeptide of FIG. 1 [SEQ ID NO:2], means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 1 [SEQ ID NO:2] may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of FABI set out in FIG. 1 [SEQ ID NO:2] variants, analogs, derivatives and fragments thereof, and variants, analogs and derivatives of the fragments. Alternatively, particularly preferred embodiments of the invention in this regard are polypeptides having the amino acid sequence of the FABI, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the FABI polypeptide of FIG. 1 [SEQ ID NO:2] in which several, a few, 5 to 10, 1 to 5, 1 to 3, 2, 1 or no amino acid residues are substituted deleted or added, in any combination. Especially preferred among these are silent substitutions, additions and deletions, which do not alter the properties and activities of the FABI. Also especially preferred in this regard are conservative substitutions. Most highly preferred are polypeptides having the amino acid sequence of FIG. 1 [SEQ ID NO:2] without substitutions.

The polypeptides and polynucleotides of the present invention are preferably provided in an isolated form, and preferably are purified to home.

The polypeptides of the present invention include the polypeptide of SEQ ID NO:2 (in particular the mature polypeptide) as well as polypeptides which have at least 80% identity to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of FABI, most particularly fragments of FABI having the amino acid set out in FIG. 1 [SEQ D NO:2] and fragments of variants and derivatives of the FABI of FIG. 1 [SEQ ID NO:2].

In this regard a fragment is a polypeptide having an amino acid sequence that entirely is the same as part but not all of the amino acid sequence of the aforementioned FABI polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a FABI polypeptide of the present comprised within a precursor polypeptide designed for expression in a host and having heterologous pre and pro-polypeptide regions fused to the amino terminus of the FABI fragment and an additional region fused to the carboxyl terminus of the fragment. Therefore, fragments in one aspect of the meaning intended herein, refers to the portion or portions of a fusion polypeptide or fusion protein derived from FABI.

Particularly preferred fragments include those encoded by amino acids 1–20, 21–40, 41–60, 61–80, 81–100, 101–120, 121–140, 141–160, 161–180, 181–200, 201–220, 221–240, 241–256 and contiguous combinations thereof.

More particularly preferred fragments include, for example, those with high homology to other sequenced structurally related elements. These include, for example, regions homologous to fragments of *E. coli* fabI including about 13 to about 25, about 32 to about 39, about 112 to about 125, about 156 to about 196 and about 231 to about 252. Among especially preferred fragments of the invention are truncation mutants of FABI. Truncation mutants include FABI polypeptides having the amino acid sequence of FIG. 1 [SEQ ID NO:2] or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally. Degradation products of the polypeptides of the invention in a host cells particularly a staphylococcus, are also preferred polypeptides.

Also preferred in this aspect of the invention are fragments characterized by structural or functional attributes of FABI. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of FABI.

Among the preferred fragments in this regard are those that comprise regions of FABI that contain structural features, such as the features set out above. In this regard, the regions defined by the residues 1 to about 8, about 26 to about 34, about 39 to about 61, about 70 to about 80, about 95 to about 107, about 127 to about 139, about 162 to about 173 and about 207 to about 220 are characterized by amino acids believed to comprise alpha helix forming regions. Additionally, the regions defined by the residues about 9 to about 13, about 19 to about 25, about 62 to about 69, about 85 to about 95, about 141 to about 156, about 173 to about 188 about 220 to about 226, about 232 to about 240 are characterized by residues believed to comprise beta-sheet regions. Also, the regions defined by the residues about 80 to about 85, about 108 to about 112, about 120 to about 125, about 178 to about 183, and about 198 to about 203 are characterized by regions belived to comprise turn regions. Also, the regions defined by the residues about 80 to about 85, about 105 to about 110, about 120 to about 125, about 138 to about 143, about 145 to about 153, about 175 to about 180, about 187 to about 192, and about 240 to about 245 are characterized by amino acid compositions believed to comprise coil regions. The regions defined by the residues about 9 to about 14, about 20 to about 36, about 86 to about 98, about 115 to about 129, about 138 to about 152, about 161 to about 179, about 185 to about 195, about 226 to about 240, about 249 to about 256 are characterized by hydrophobic amino acids. Additionally, the regions defined by the residues about 2 to about 8, about 14 to about 19, about 36 to about 86, 98 to about 115, about 130 to about 138, about 152 to about 161, about 180 to about 186, about 206 to about 226, about 239 to and about 249 are characterized by hydrophilic amino acids. Also, the regions defined by the residues about 20 to about 40, about 43 to about 62, about 72 to about 93, about 102 to about 117, about 128 to about 140, about 180 to about 220, and about 228 to about 240 are characterized by amino acid residues believed to comprise an alpha amphipathic region and the regions defined by the residues about 1 to about 10, about 27 to about 50, about 60 to about 72, about 97 to about 110, about 158 to about 191, about 208 to about 220, and about 240 to about 252 are characterized by amino acid reside believed to comprise a beta amphipathic region. Additionally, the regions defined by the residues about 38 to 58, about 77 to about 89, about 98 to about 114, about 130 to about 142, about 190 to about 204, about 208 to about 230, and about 234 to about 246 are characteristics of amino acid residues believed to comprise flexible regions. The regions defined by residues about 34 to about 62, about 98 to about 112 and about 206 to about 222 are believed to comprise surface forming regions. Additionally, the regions defined by residues about 3 to about 9, about 14 to about 20, about 25 to about 33, about 38 to about 60, about 65 to about 88, about 98 to about 114, about 120 to about 124, about 130 to about 140, about 178 to about 185, about 195 to about 228, and about 236 to about 247 are believed to comprise regions of high antigenicity. Such regions set forth above may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of FABI. Most highly preferred in this regard are fragments that have a chemical, biological or other activity of FABI, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIG. 1 [SEQ ID NO:2], which include *E. coli* Enoyl (ACP) reductase, FabI. Among particularly preferred fragments in these regards are truncation mutants, as discussed above. Further preferred polynucleotide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, Host Cells, Expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced indepently, co-introduced or introduced joined to the polynucleotides of the invention.

Thus for instance, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenovixuses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al., (1989) *MOLECULAR CLONING. A LABORATORY MANUAL*, 2nd Ed.; Cold Spring Harbor Laboratory Press, Cold Spring Harbor, N.Y.

The DNA sequence in the expression vector is operatively link to appropriate expression control sequence(s), including, for instance a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other prokaryotes.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as streptoccoi, staphylococci, *E. coli*, streptomyces and *Salmonella typhimurium* cells; fungal cells, such as yeast cells and Aspergillus cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be affected by calcium phosphate transfection, DEAE-dextran mediated transfection, cationic lipid-mediated transfection, electroporation, transduction, scrape loading, ballistic introduction, infection or other methods. Such methods are described in many standard laboratory manuals, such as Davis et al, (1986) *BASIC METHODS IN MOLECULAR BIOLOGY*, and Sambrook et al., (1989) *MOLECULAR CLONING: A LABORATORY MANUAL*, 2nd Ed., Cold Spring Harbor Laboratory Press, Cold Spring Harbor, N.Y.

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention Appropriate cloning and expression vectors for use with prokaryotic and eukaryotic hosts are described by Sambrook et al., (1989) *MOLECULAR CLONING: A LABORATORY MANUAL*, 2nd Ed., Cold Spring Harbor Laboratory Press, Cold Spring Harbor, N.Y.

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trp1 gene of *S. cerevisiae*.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhances.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunolglobulin that is useful to solubilize or purify polypeptides. For example, EP-A-O 464 533 (Canadian counterpart 2045869) discloses fusion proteins comprising various portions of constant region of immunoglobin molecules together with another human protein or part thereof. In many cases, the Fc part in fusion protein is thoroughly advantageous for use in therapy and diagnosis and thus results, for example, in improved pharmacokinetic properties (see EP-A 0232 262). On the other hand, for some uses it would be desirable to be able to delete the Fc part after the fusion protein has been expressed, detected and purified in the advantageous manner described. This is the case when Fc portion proves to be a hindrance to use in assays, therapy or diagnosis, for example when the fusion protein is to be used as antigen for immunizations. In drug discovery, for example, human proteins, such as, shIL5- has been fused with Fc portions for the purpose of high-throughput screening assays to identify antagonists of hIL-5. See, D. Bennett et al, (1995) *Journal of Molecular Recognition*, Vol. 8 52–58 and K. Johanson et al, (1995) *The Journal of Biological Chemistry*, Vol. 270, No. 16, pp 9459–9471.

Suitable prokaryotic hosts for propagation, maintenance or expression of polynucleotides and polypeptides in accordance with the invention include streptococci, *Escherichia coli, Bacillus subtilis* and *Salmonella typhimurium*. Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis. USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means,and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al, (1981) *Cell* 23: 175. Other cell lines capable of expressing a compatible vector include for example, the C127, 3T3, CHO, HeLa, human kidney 293 and BHK cell lines.

Mammalian expression vectors may comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

FABI polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification this invention also provides the use of anti-FABI antibodies for detection of FABI during purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

FABI polynucleotides and polypeptides may be used in accordance with the present invention for a variety of applications, particularly those that make use of the chemical and biological properties of FABI, Additional applications relate to diagnosis and to treatment of disorders of cells, tissues and organisms. These aspects of the invention are illustrated further by the following discussion.

Polynucleotide Assays

This invention is also related to the use of the FABI polynucleotides to detect complementary polynucleotides such as, for example, as a diagnostic reagent. Detection of FABI in a eukaryote, particularly a mammal, and especially a human, will provide a diagnostic method that can add to, define or allow a diagnosis of a disease. Eukaryotes (herein also "individual(s)"), particularly mammals, and especially humans, carrying a FABI gene may be detected at the DNA level by a variety of techniques. Nucleic acids for diagnosis may be obtained from an individual's cells and tissues, such as bone, blood, muscle, cartilage, and skin. Tissue biopsy and autopsy material is also preferred for samples from an individual to use in a diagnostic assay. Genomic DNA may be used directly for detection or may be amplified enzymatically by using PCR prior to analysis. PCR (Saiki et al., (1986) *Nature*, 324: 163–166). RNA or cDNA may also be used in the same ways. As an example, PCR primers complementary to the nucleic acid encoding FABI can be used to identify and analyze FABI presence and expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled FABI RNA or alternatively, radiolabeled FABI antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., (1985) *Science*, 230: 1242).

Sequence changes at specific locations also may be revealed by nuclease protection assays, such as RNase and S1 protection or the chemical cleavage method (e.g., Cotton et al., (1985) *Proc. Natl. Acad. Sci., USA*, 85: 4397–4401).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

A mutation may be ascertained for example, by a DNA sequencing assay. Samples are processed by methods known in the art to capture the RNA. First strand cDNA is synthesized from the RNA samples by adding an oligonucleotide primer consisting of sequences which hybridize to a region on the mRNA. Reverse transcriptase and deoxynucleotides are added to allow synthesis of the first strand cDNA. Primer sequences are synthesized based on the DNA sequence of the FABI protein of the invention. The primer sequence is generally comprised of at least 15 consecutive bases, and may contain at least 30 or even 50 consecutive bases.

Cells carrying mutations in the gene of the present invention may also be detected at the DNA level by a variety of techniques, to allow for serotyping, for example. Nucleic acids for diagnosis may be obtained from an individual's cells or bodily fluids, including but not limited to blood, urine, saliva, tissue biopsy and autopsy material. The genomic DNA may be used directly for detection or may be amplified enzymatically by using PCR (Saiki et al., (1986) *Nature*, 324:163–166) prior to analysis. RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding FABI can be used to identify and analyze mutations. Examples of representative primers are shown below in Table 1. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

individual such that the gene may then be subject to various techniques for elucidation of the DNA sequence. In this way, mutations in the DNA sequence may be determined, for example, to ascertain the serotype of the organism.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genotyping based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., (1985) *Science*, 230:1242).

Sequence changes at specific locations may also be revealed by nuclease protection assays, such as RNase and S1 protection or the chemical cleavage method (e.g., Cotton et al., (1985) *PNAS, USA*, 85:4397–4401).

Thus, the detection of a specific DNA sequence and/or quantitation of the level of the sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA. The invention provides a process for diagnosing disease, particularly bacterial infections, and most particularly staphylococcal infections, comprising determining from a sample derived from an individual an increased level of expression of polynucleotide having the sequence of FIG. 2 [SEQ ID NO:1]. Increased expression of polynucleotide can be measured using any on of the methods well known in the art for the quantation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Polypeptide Assays

The present invention also relates to a diagnostic assays such as quantitative and diagnostic assays for detecting

TABLE 1

Primers used for detection of mutations in FAB I gene

| SEQ ID NO: | SEQUENCE |
|---|---|
| 3 | 5'-CGCCTCGAGATGTTAAATCCTGAAAACAAAACATATGTC-3' |
| 4 | 5'-CGCGGATCCAATCAAGTCAGGTTGAAATATCCA-3' |

The above primers may be used for amplifying FABI DNA isolated from a sample derived from an individual. The invention also provides the primers of Table 1 with 1, 2, 3 or 4 nucleotides removed from the 5' and/or the 3' end. The primers may be used to amplify the gene isolated from the levels of FABI protein in cells and tissues, including determination of normal and abnormal levels. Thus, for instance, a diagnostic assay in accordance with the invention for detecting a pathological expression level of FABI protein compared to normal control tissue samples may be used to detect the presence of bacterial infection, for example. Assay technique that can be used to determine levels of a protein, such as an FABI protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to FABI, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any FABI proteins attached to the polystyrene dish. Unbound monoclonal antibody is washed out with buffer. The reporter antibody linked to horseradish peroxidase is placed in the dish resulting in binding of the reporter antibody to any monoclonal antibody bound to FABI, Unattached reporter antibody is then washed out. Reagents for peroxidase activity, including a colorimetric substrate are then added to the dish. Immobilized peroxidase, linked to FABI through the primary and secondary antibodies, produces a colored reaction product. The amount of color developed in a given time period indicates the amount of FABI protein present in the sample. Quantitative results typically are obtained by reference to a standard curve A competition assay may be employed wherein antibodies specific to FABI attached to a solid support and labeled FABI and a sample derived from form an individual are passed over the solid support and the amount of label detected attached to the solid support can be correlated to a quantity of FABI in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an individual or by administering the polypeptides to an individual, preferably a nonhuman. The antibody so obtained will then bind the polypeptides itself. In this manner, even a sequence encoding only a fragment of the polypeptides can be used to generate antibodies binding the whole native polypeptides. Such antibodies can than be used to isolate the polypeptide from tissue expressing that polypeptide.

For preparation of monoclonal antibodies, any technique which provides antibodies produced by continuous cell line cultures can be used. Examples include the hybridoma technique (Kohler, G. et al., (1975) *Nature* 256: 495–497, the trioma technique, the human B-cell hybridoma technique (Kozbor et al., (1983) *Immunology Today* 4: 72 and the EBV-hybridoma technique to produce human monoclonal antibodies (Cole et al, (1985) in *Monoclonal Antibodies And Cancer Therapy*, Alan R. Liss, Inc. pp. 77–96.

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Polypeptide derivatives include antigenically or immunologically equivalent derivatives which form a particular aspect of this invention.

The term "antigenically equivalent derivative" as used herein encompasses a polypeptide or its equivalent which will be specifically recognised by certain antibodies which, when raised to the protein or polypeptide according to the present invention, interfere with the immediate physical interaction between pathogen and mammalian host.

The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the the protein or polypeptide, or an antigenically or immunologically equivalent polypeptide thereof may be sufficiently antigenic to improve immunogenicity so as to obviate the use of a carrier.

Using the procedure of Kohler et al, (1975) *Nature* 256, 495–497), antibody-containing cells from the immunised mammal are fused with myeloma cells to create hybridoma cells secreting monoclonal antibodies.

The hybridomas are screened to select a cell line with high binding affinity and favorable cross reaction with other staphylococcal species using one or more of the original polypeptide and/or the fusion protein. The selected cell line is cultured to obtain the desired Mab.

Hybridoma cell lines secreting the monoclonal antibody are another aspect of this invention.

Alternatively phage display technology could be utilised to select antibody genes with binding activities towards the polypeptide either from repertoires of PCR amplified v-genes of lymphocytes from humans screened for possessing anti-Fbp or from naive libraries (McCafferty, J. et al., (1990), *Nature* 348, 552–554; Marks, J. et al., (1992) *Biotechnology* 10, 779–783). The affinity of these antibodies can also be improved by chain shuffling (Clackson, T. et al., (1991) *Nature* 352, 624–628).

The antibody should be screened again for high affinity to the polypeptide and/or fusion protein.

The above-described antibodies may be employed to isolate or to identify clones expressing the polypeptide or purify the polypeptide of the present invention by attachment of the antibody to a solid support for isolation and/or purification by affinity chromatography.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, traumatic, chemical or thermal damage or by implantation of indwelling devices, or wounds in the mucous membranes, such as the mouth, mammary glands, urethra or vagina.

The polypeptides or cells expressing them can be used as an immunogen to produce antibodies thereto. These antibodies can be, for example, polyclonal or monoclonal antibodies. The term antibodies also includes chimeric, single chain, and humanized antibodies, as well as Fab fragments, or the product of an Fab expression library. Various procedures known in the art may be used for the production of such antibodies and fragments.

Antibodies generated against the polypeptides of the present invention can be obtained by direct injection of the polypeptides into an individual or by administering the polypeptides to an individual, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

As mentioned above, a fragment of the final antibody may be prepared.

The antibody may be either intact antibody of $M_r$ approx 150,000 or a derivative of it, for example a Fab fragment or a Fv fragment as described in Skerra, A and Pluckthun. A (1988) Science 240 1038–1040. If two antigen binding domains are present each domain may be directed against a different epitope—termed 'bispecific' antibodies.

The antibody of the invention may be prepared by conventional means for example by established monoclonal antibody technology (Kohler, G. et al (1975), Nature 256, 495–497) or using recombinant means e.g. combinatorial libraries, for example as described in Huse, W. D. et al., (1989) Science 246, 1275–1281.

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or Streptomyces sp. or a eukaryotic cell, such as a mouse C127, mouse myeloma, human HeLa, Chinese hamster ovary, filamentous or unicellular fungi or insect cell. The host may also be a transgenic animal or a transgenic plant, for example as described in Hiatt, A et al, (1989) Nature 34, 76–78. Suitable vectors include plasmids, bacteriophages, cosmids and recombinant viruses, derived from, for example, baculoviruses and vaccinia.

The Fab fragment may also be prepared from its parent monoclonal antibody by enzyme treatment, for example using papain to cleave the Fab portion from the Fc portion.

Preferably the antibody or derivative thereof is modified to make it less immunogenic in the individual. For example, if the individual is human the antibody may most preferably be 'humanised'; where the complimentarity determining region(s) of the hybridoma-derived antibody has been transplanted into a human monoclonal antibody, for example as described in Jones, P. et al. (1986), Nature 321, 522–525 or Tempest et al., (1991) Biotechnology 9, 266–273.

The modification need not be restricted to one of 'humanisation'; other primate sequences (for example Newman, R. et al., 1992, Biotechnology 10, 1455–1460) may also be used.

The humanised monoclonal antibody, or its fragment having binding activity, form a particular aspect of this invention.

This invention provides a method of screening drugs to identify those which interfere with the interaction of the FABI protein or active fragment to mammalian cells, the method comprising incubating a mammalian cell or membrane preparation with labeled polypeptide in the presence of the drug and measuring the ability of the drug to block this interaction.

The use of a polynucleotide of the invention in genetic immunization will preferably employ a suitable delivery method such as direct injection of plasmid DNA into muscles (Wolff et al., (1992) Hum. Mol Genet, 1:363, Manthorpe et al., (1963) Hum. Gene Ther. 4, 419), delivery of DNA complexed with specific protein carriers (Wu, et al, (1989) J Biol Chem 264, 16985), coprecipitation of DNA with calcium phosphate (Benvenisty & Reshef, PNAS, 1986:83,9551), encapsulation of DNA in various forms of liposomes (Kaneda et al., (1989) Science 243, 375), particle bombardment (Tang et al., (1992) Nature 356:152, Eisenbraun et al., (1993) DNA Cell Biol 12:791) and in vivo infection using cloned retroviral vectors (Seeger et al., (1984) PNAS 81, 5849). Suitable promoters for muscle transfection include CMV, RSV, SRa, actin, MCK, alpha globin, adenovirus and dihydrofolate reductase.

Thus, among others, antibodies against FABI nay be employed to inhibit FAS or FABI enzymatic activity or FABI expression.

FABI may also be employed to inhibit infections including, but not limited to infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellutitis, wound infection, bacterial myositis), and bone and joint (e.g. septic arthritis, osteomyelitis).

FABI may also be employed to treat bacterial infection, such as, for example, infections of upper respiratory tract (e.g. otitis media, bacterial tracheitis, acute epiglottitis, thyroiditis), lower respiratory (e.g. empyema lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis).

FABI Binding Molecules and Assays

This invention also provides a method for identification of molecules, such as binding molecules, that bind FABI. Genes encoding proteins that bind FABI, such as binding proteins, can be identified by numerous methods known to those of skill in the art. Examples of such methods are described in many laboratory manuals such as, for instance, Coligan et al., (1991) Current Protocols in Immunology 1(2): Chapter 5.

For instance, expression cloning may be employed for this purpose. To this end, to isolate genes in an individual which are responsive to FABI, polyadenylated RNA is prepared from a cell responsive to FABI, a cDNA library is created from this RNA, the library is divided into pools and the pools are transfected individually into cells that are not responsive to FABI. The transfected cells then are exposed to labeled FABI. (FABI can be labeled by a variety of well-known techniques including standard method of radio-iodination or inclusion of a recognition site for a site-specific protein kinase.) Following exposure, the cells are fixed and binding of FABI is determined. These procedures conveniently are carried out on glass slides.

Alternatively a labeled ligand can be photoaffinity linked to a cell extract, such as a membrane or a membrane extract, prepared from cells that express a molecule that it binds, such as a binding molecule. Cross-linked material is resolved by polyacrylamide gel electrophoresis ("PAGE") and exposed to X-ray film. The labeled complex containing the ligand-binding can be excised, resolved into peptide fragments, and subjected to protein microsequencing. The amino acid sequence obtained from microsequencing can be used to design unique or degenerate oligonucleotide probes to screen cDNA libraries to identify genes encoding the putative binding molecule.

Polypeptides of the invention also can be used to assess FABI binding capacity of FABI binding molecules, such as binding molecules, in cells or in cell-free preparations.

Antagonists and Agonists—Assays and Molecules

The invention also provides a method of screening compounds to identify those which enhance or block the action of FABI on cells, such as its interaction with FABI-binding molecules such as binding molecules. An antagonist is a compound which decreases the natural biological functions of FABI. An agonists is a compound which increases the natural biological functions of FABI.

For example, a cellular component, such as a membrane, cell envelope or cell wall, or a preparation of any thereof, may be prepared from a cell that expresses a molecule that binds FABI, such as a molecule of a physiological pathway modulated or affected by FABI, such as, for example, a regulatory pathway, such as a FAS pathway. The preparation is incubated with labeled FABI in the absence or the presence of a candidate molecule which may be a FABI agonists or antagonist. The ability of the candidate molecule to bind the binding molecule is reflected in decreased binding of the labeled ligand. Molecules which bind gratuitously, i.e., without inducing the effects of FABI on binding the FABI binding molecule, are most likely to be good antagonists. Molecules that bind well and elicit effects that are the same as or closely related to FABI are agonists.

FABI-like effects of potential agonists and antagonists may by measured, for instance by determining activity of a second messenger system following interaction of the candidate molecule with a cell or appropriate cell preparation, and comparing the effect with that of FABI or molecules that elicit the same effects as FABI. Second messenger systems that may be useful in this regard include but are not limited to AMP guanylate cyclase, ion channel or phosphoinositide hydrolysis second messenger systems.

Another example of an assay for FABI antagonists is a competitive assay that combines FABI and a potential antagonist with membrane-bound FABI binding molecules or recombinant FABI binding molecules under appropriate conditions for a competitive inhibition assay. FABI can be labeled, such as by radioactivity, such that the number of FABI molecules bound to a binding molecule can be determined accurately to assess the effectiveness of the potential antagonist.

A further example of a screen is a detect the reduction of crotonyl-CoA by measuring the consumption of NADH. Crotonyl-ACP may also be used in place of crotonyl-CoA in such a screen. Test compound are added to the reaction mix to determine the effect on the reduction of crotonyl-CoA or crotonyl-ACP. Agonists can be identified if the level of reduction is increased and antagonists can be identified if the level of reduction is decreased. Diazaborine or palmitoyl CoA may be used as a positive control for antagonism. It is preferred that these screens be used in a highthrouput assay using a microtitre plate format and a plate reader.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing FABI-induced activities, thereby preventing the action of FABI by excluding FABI from binding.

Potential antagonists include a small molecule which binds to and occupies the binding site of the polypeptide thereby preventing binding to cellular binding molecules, such as binding molecules, such that normal biological activity is prevented. Examples of small molecules include but are not limited to small organic molecules, peptides or peptide-like molecules.

Potential antagonists also include diazaborine mimics (Boron substituted for sulphur, carbon, or oxygen) and mimic of activated isoniazid.

Other potential antagonists include antisense molecules. Antisense technology can be used to control gene expression through antisense DNA or RNA or through triple-helix formation. Antisense techniques are discussed, for example, in—Okano, J. (1991) *Neurochem*. 56:560; *OLIGODEOXY-NUCLEOTIDES AS ANTISENSE INHIBITORS OF GENE EXPRESSION*, CRC Press, Boca Raton, Fla., (1988). Triple helix formation is discussed in, for instance Lee et al., (1979) *Nucleic Acids Research* 6: 3073; Cooney et al., (1988) *Science* 241: 456; and Dervan et al., (1991) *Science* 251: 1360. The methods are based on binding of a polynucleotide to a complementary DNA or RNA For example, the 5' coding portion of a polynucleotide that encodes the mature polypeptide of the present invention may be used to design an antisense RNA oligonuclectide of from about 10 to 40 base pairs in length. A DNA oligonucleotide is designed to be complementary to a region of the gene involved in transcription thereby preventing transcription and the production of FABI. The antisense RNA oligonucleotide hybridizes to the mRNA in vivo and blocks translation of the mRNA molecule into FABI polypeptide. The oligonucleotides described above can also be delivered to cells such that the antisense RNA or DNA may be expressed in vivo to inhibit production of FABI.

The antagonists may be employed in a composition with a pharmaceutically acceptable carrier, e.g., as hereafter described.

The antagonists may be employed for instance to inhibit diseases including, but not limited to infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacteral myositis), and bone and joint (e.g. septic arthritis, osteomyelitis).

In a particular aspect the invention provides the use of the polypeptide, polynucleotide or inhibitor of the invention to interfere with the immediate physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block FABI protein mediated mammalian cell invasion by, for example, initiating phosphorylation of mammalian tyrosine kinases (Rosenshine et al., (1992) *Infect. Immun.* 60, 2211–7); iii) to block bacterial adhesion between mammalian extracellular matrix proteins and bacterial FABI proteins which mediate tissue damage; and/or iv) to block the normal progression of pathogenesis in infections initiated other than by the implantation of in-dwelling devices or by other surgical techniques.

The antagonists may be employed in a composition with a pharmaceutically acceptable carrier, e.g., as hereinafter described.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

In view of the conservation in the amino acid sequence of FABI with known enzymes in *H. influenzae*, *E. coli* and *S. typhimurium*, an antibacterial targeted at FABI agonist and antagonist compounds provided by the invention are believed to be active against a wide variety of Gram negative and positive organisms. In addition, a FabI homolog (InhA) has been identified in *Mycobacterium tuberculosis*. Therefore, an antibacterial provided by the invention, targeted at FABI, may also have anti-mycobacterial activity. Further, since Diazaborine derivatives inhibit LPS biosynthesis (Lam et al (1987) *J. Antimicrob. Chemother.* 20 37–45) and LPS is a known virulence factor, the invention provides antibacterial compounds targeted at FABI that have enhanced activity in vivo.

Vaccines

Another aspect of the invention relates to a method for inducing an immunological response in a mammal which comprises inoculating the mammal with FABI, or a fragment or variant thereof, adequate to produce antibody to protect said animal from disease, particularly a bacterial infection, and especially a staphylococcal infection. Yet another aspect of the invention relates to a method of inducing immunological response in a mammal which comprises, through gene therapy, delivering gene encoding FABI, or a fragment or a variant thereof, for expressing FABI, or a fragment or a variant thereof in vivo in order to induce an immunological response to produce antibody to protect said animal from disease.

A further aspect of the invention relates to an immunological composition which, when introduced into a mammalian host, induces an immunological response in that mammal to a given FABI or protein coded therefrom, wherein the composition comprises a recombinant FABI or protein coded therefrom comprising DNA which codes for and expresses an antigen of said gene or protein coded therefrom.

FABI or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Included in the present invention are methods for the introduction into an individual polypeptides or polynucleotides of the invention along with an immunostimulatory DNA sequence to enhance the immune response to FABI, and compositions comprising FABI and an immunostimulatory DNA sequence. Such immunostimulatory DNA sequences ane their uses are described in Sato, et al., (1996) *Science* 273: 352.

The present invention also includes a vaccine formulation which comprises the immunogenic recombinant protein together with a suitable carrier. Since the protein may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Whilst the invention has been described with reference to certain FABI, it is to be understood that this covers fragments of the naturally occurring protein and similar proteins (for example, having sequence homologies of 50% or greater) with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Also provided by the invention are diagnostic kits for the FABI gene and homologs will enable the directed therapy of a FABI directed antibacterial. DNA hybridisation or protein (monoclonal antibody) based kits for the identification of FabI and homologs of FABI from different species. Such a kit could also detect mutations in the FABI gene/protein and its homologs.

Administration

Polypeptides and other compounds of the present invention may be employed alone or in conjunction with other compounds, such as therapeutic compounds.

The pharmaceutical compositions may be administered in any effective, convenient manner including, for instance administration by topical oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to a individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to human individuals, it is expected that the daily dosage level of the active agent will be from 0.01 to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent staphylococcal wound infections.

Many orthopaedic surgeons consider that individuals with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 $\mu$g/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 $\mu$g/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of bacteria containing the FABI protein.

In order to facilitate understanding of the following example certain frequently occurring methods and/or terms will be described.

Gene Therapy

The FABI polynucleotides, polypeptides, agonists and antagonists that are polypeptides may be employed in accordance with the present invention by expression of such polypeptides in vivo, in treatment modalities often referred to as "gene therapy." The compounds of the inventions may be used as gene immunotherapies, to engender an immune response in an individual against the organism from which such compound was derived as well as related organisms.

Thus, for example, cells from an individual may be engineered with a polynucleotide, such as a DNA or RNA, encoding a polypeptide ex vivo, and the engineered cells then can be provided to an individual to be treated with the polypeptide. For example, cells may be engineered ex vivo by the use of a retroviral plasmid vector containing RNA among a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to an individual for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., (1989) *Biotechniques* 7: 980–990, or any other proper (e.g., cellular promoters such as eukaryotic cellular promoters including, but not limited to, the histone, RNA polymerase III, aid β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the RSV promoter; inducible promoters, such as the MMT promoter, the metallothionein promoter; heat shock promoters; the albumin promoter; the ApoAI promoter; human globin promotes; viral thymidine kinase promoters, such as the Herpes Simplex thymidine kinase promoter, retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., (1990) *Human Gene Therapy* 1: 5–14. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain teams used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., (1989) *MOLECULAR CLONING: A LABORATORY MANUAL*, 2nd Ed; Cold Spring Harbor Laboratory Press, Cold Spring Harbor, N.Y.

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook et al., *MOLECULAR CLONING: A LABORATORY MANUAL*, 2nd Ed., Cold Spring Harbor Laboratory Press, Cold Spring Harbor, N.Y. (1989) and numerous other references such as, for instance, by Goeddel et al., (1980) *Nucleic Acids Res.* 8: 4057.

Unless described otherwise, ligations were accomplished using standard buffers, incubation temperatures and times, approximately equimolar amounts of the DNA fragments to be ligated and approximately 10 units of T4 DNA ligase ("ligase") per 0.5 µg of DNA.

Example 1

Isolation and Sequencing of *S. aureus* FABI Gene

The polynucleotide having the DNA sequence given in SEQ ID NO:1 was obtained from the sequencing of a library of clones of chromosomal DNA of *S. aureus* WCUH 29 in *E. coli*. It has been demonstrated by the process herein described that it is transcribed in vivo in an established infection of *S. aureus* WCUH 29 in a mouse model of infection.

To obtain the polynucleotide encoding FABI protein using the DNA sequence given in SEQ ID NO:1 typically a library of clones of chromosomal DNA of *S. aureus* WCUH 29 in *E. coli* or some other suitable host is probed with a radiolabelled oligonucleotide, preferably a 17 mer or longer, derived from the partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., (1989) *MOLECULAR CLONING, A LABORATORY MANUAL*, 2nd Ed.; Cold Spring Harbor Laboratory Press, Cold Spring Harbor, N.Y. (see Screening By Hybridization 1.90 and Sequencing Denatured Double-Stranded DNA Templates 13.70).

In some cases the sequencing data from two or more clones containing overlapping *S. aureus* WCUH 29 DNA was used to construct the contiguous DNA sequence in SEQ ID NO:1. Libraries may be prepared Libraries may be prepared by routine methods, for example: Methods 1 and 2

Total cellular DNA is isolated from *Staphylococcus aureus* strain WCUH 29(NCIMB 40771) according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolysed with a combination of four restriction enzymes (RsaI, PalI, AluI and Bsh1235I) and size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

FABI Enzyme Activity Analysis

The activity of FABI protein may be measured using either crotonoyl-CoA or crotonoyl-ACP as a substrate (Bergler, et al, (1994), *J. Biol. Chem.* 269, 5493–5496) and monitoring the decrease in absorbance at 340 nm due to the consumption of NADH. Crotonoyl-ACP (Km 22 uM) is a better substrate than crotonoyl-CoA (Km 2.7 mM), crotonoyl-CoA is available from Sigma (C6146). A diazaborine derivative may be used as a positive control, this should be readily available via a 2 step synthesis with publicly available starting materials using methods known in the art. Test compounds may be added to this assay to determine whether they agonize or antagonize enzymatic activity.

Example 3

Gene Immunotherapeutic Expression of *S. aureus* FABI

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

FABI DNA capable of expressing active FABI, is isolated. The ends of the fragment are modified, if necessary, for cloning into the vector. For instance 5' overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the FABI fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the FABI gene is introduced into the packaging cells by standard techniques. Infectious viral particles containing the FABI gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate traction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce FABI product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated polypeptide comprising the amino acid sequence set forth in SEQ ID NO:2.

2. A composition comprising the isolated polypeptide of claim 1 and an acceptable carrier.

3. The isolated polypeptide of claim 1, wherein the isolated polypeptide comprises a heterologous amino acid sequence fused to the amino acid sequence set forth in SEQ ID NO:2.

4. A composition comprising the isolated polypeptide of claim 3 and an acceptable carrier.

5. The isolated polypeptide of claim 1, wherein the isolated polypeptide consists of the amino acid sequence set forth in SEQ ID NO:2.

6. A composition comprising the isolated polypeptide of claim 5 and an acceptable carrier.

7. An isolated polypeptide fragment comprising at least 50 consecutive amino acids of SEQ ID NO: 2 wherein said polypeptide fragment comprises the amino acid at position 191 of SEQ ID NO: 2, wherein said amino acid is glycine or a conservative substitution thereof, and wherein the polypeptide fragment comprises at least one biological activity of FabI.

8. The isolated polypeptide fragment of claim 7, wherein the isolated polypeptide fragment comprises a heterologous amino acid sequence fused to the at least 50 consecutive amino acids of SEQ ID NO:2.

9. An isolated polypeptide fragment comprising at least 30 consecutive amino acids of SEQ ID NO: 2 wherein said polypeptide fragment comprises the amino acid at position 191 of SEQ ID NO: 2, wherein said amino acid is glycine or a conservative substitution thereof, and wherein the polypeptide fragment comprises at least one biological activity of FabI.

10. The isolated polypeptide fragment of claim 9, wherein the isolated polypeptide fragment comprises a heterologous amino acid sequence fused to the at least 30 consecutive amino acids of SEQ ID NO:2.

11. An isolated polypeptide, wherein said polypeptide comprises an amino acid sequence encoded by a polynucleotide that hybridizes under stringent conditions to the complementary strand of a polynucleotide having SEQ ID NO: 1 wherein said polypeptide is capable of reducing crotonyl-CoA or crotonyl-ACP and wherein said polypeptide comprises the amino acid at position 191 of SEQ ID NO: 2, or its equivalent, and said amino acid is glycine or a conservative substitution thereof.

12. An isolated polypeptide comprising an amino acid sequence having at least 95% identity with the amino acid sequence set forth in SEQ ID NO: 2 wherein said polypeptide is capable of reducing crotonyl-CoA or crotonyl-ACP, wherein said polypeptide comprises the amino acid at position 191 of SEQ ID NO: 2 wherein said polypeptide is capable of reducing crotonyl-CoA or crotonyl-ACP, or its equivalent, and said amino acid is glycine or a conservative substitution thereof.

13. An isolated polypeptide, comprising an amino acid sequence comprising SEQ ID NO: 2 with 0 to 10 conservative amino acid substitutions wherein said polypeptide is capable of reducing crotonyl-CoA or crotonyl-ACP, wherein said polypeptide comprises the amino acid at position 191 of SEQ ID NO: 2, or its equivalent, and said amino acid is glycine or a conservative substitution thereof.

* * * * *

UNITED STATES PATENT AND TRADEMARK OFFICE
CERTIFICATE OF CORRECTION

PATENT NO.     : 6,753,172 B1
DATED          : June 22, 2004
INVENTOR(S)    : Payne et al.

It is certified that error appears in the above-identified patent and that said Letters Patent is hereby corrected as shown below:

Column 43,
Lines 51-55, please replace:
"comprises the amino acid at position 191 of SEQ ID NO:2, wherein said acid is glycineora conservative substitution thereof, and wherein the polypeptide fragment comprises at least one biological activity of FabI." with -- is capable of reducing crotonyl-CoA or crotonyl-ACP. --

Column 43, line 62 - Column 44, line 34,
Please replace "comprises the amino acid at position 191 of SEQ ID NO: 2, wherein said amino acid is glycine or a conservative substitution thereof, and wherein the polypeptide fragment comprises at least one biological activity of FabI." with -- is capable of reducing crotonyl-CoA or crotonyl-ACP. --

Column 44,
Lines 41-47, "that hybridizes under stringent conditions to the complementary strand of a polynucleotide having SEQ ID NO: 1 wherein said polypeptide is capable of reducing crotonyl-CoA or crotonyl-ACP and wherin said polypeptide comprises the amino acid sequence at position 191 of SEQ ID NO: 2, or its equivalent, and said amino acid is glycine or a conservative substitution thereof." with-- having at least 95% identity with the polynucleotide sequence set forth in SEQ ID NO: 1 wherein said polypeptide is capable of reducing crotonyl-CoA or crotonyl-ACP. --
Lines 52-56, please delete "wherein said polypeptide comprises the amino acid at position 191 of SEQ ID NO: 2, wherein said polypeptide is capable of reducing crotonyl-CoA or crotonyl-ACP, or its equivalent, and said amino acid is glycine or a conservation substitutive thereof."

UNITED STATES PATENT AND TRADEMARK OFFICE
CERTIFICATE OF CORRECTION

PATENT NO. : 6,753,172 B1
DATED : June 22, 2004
INVENTOR(S) : Payne et al.

It is certified that error appears in the above-identified patent and that said Letters Patent is hereby corrected as shown below:

Column 44, (cont'd,)
Lines 60-63, please delete "wherein said polypeptide comprises the amino acid at position 191 of SEQ ID NO: 2, or its equivalent, and said amino acid is glycine or a conservation substitution thereof."

Signed and Sealed this

Nineteenth Day of April, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 771
<212> TYPE: DNA
<213> ORGANISM: Staphylococcus aureus

<400> SEQUENCE: 1

```
atgttaaatc ttgaaaacaa aacatatgtc atcatgggaa tcgctaataa gcgtagtatt      60
gcttttggtg tcgctaaagt tttagatcaa ttaggtgcta aattagtatt tacttaccgt     120
aaagaacgta gccgtaaaga gcttgaaaaa ttattagaac aattaaatca accagaagcg     180
cacttatatc aaattgatgt tcaaagcgat gaagaggtta ttaatggttt tgagcaaatt     240
ggtaaagatg ttggcaatat tgatggtgta tatcattcaa tcgcatttgc taatatggaa     300
gacttacgcg gacgcttttc tgaaacttca cgtgaaggct tcttgttagc tcaagacatt     360
agttcttact cattaacaat tgtggctcat gaagctaaaa aattaatgcc agaaggtggt     420
agcattgttg caacaacata tttaggtggc gaattcgcag ttcaaaatta taatgtgatg     480
ggtgttgcta aagcgagctt agaagcaaat gttaaatatt tagcattaga cttaggtcct     540
gataatattc gcgttaatgc aatttcagct ggtccaatcc gtacattaag tgcaaaaggt     600
gtgggtggtt tcaatacaat tcttaaagaa atcgaagagc gtgcaccttt aaaacgtaac     660
gttgatcaag tagaagtagg taaaacagcg gcttacttrt taagtgactt atcaagtggc     720
gttacaggtg aaaatattca tgtagatagc ggattccacg caattaaata a             771
```

<210> SEQ ID NO 2
<211> LENGTH: 256
<212> TYPE: PRT
<213> ORGANISM: Staphylococcus aureus

<400> SEQUENCE: 2

```
Met Leu Asn Leu Glu Asn Lys Thr Tyr Val Ile Met Gly Ile Ala Asn
  1               5                  10                  15

Lys Arg Ser Ile Ala Phe Gly Val Ala Lys Val Leu Asp Gln Leu Gly
             20                  25                  30

Ala Lys Leu Val Phe Thr Tyr Arg Lys Glu Arg Ser Arg Lys Glu Leu
         35                  40                  45

Glu Lys Leu Leu Glu Gln Leu Asn Gln Pro Glu Ala His Leu Tyr Gln
     50                  55                  60

Ile Asp Val Gln Ser Asp Glu Glu Val Ile Asn Gly Phe Glu Gln Ile
 65                  70                  75                  80

Gly Lys Asp Val Gly Asn Ile Asp Gly Val Tyr His Ser Ile Ala Phe
                 85                  90                  95

Ala Asn Met Glu Asp Leu Arg Gly Arg Phe Ser Glu Thr Ser Arg Glu
            100                 105                 110

Gly Phe Leu Leu Ala Gln Asp Ile Ser Ser Tyr Ser Leu Thr Ile Val
        115                 120                 125

Ala His Glu Ala Lys Lys Leu Met Pro Glu Gly Gly Ser Ile Val Ala
    130                 135                 140

Thr Thr Tyr Leu Gly Gly Glu Phe Ala Val Gln Asn Tyr Asn Val Met
145                 150                 155                 160

Gly Val Ala Lys Ala Ser Leu Glu Ala Asn Val Lys Tyr Leu Ala Leu
                165                 170                 175
```

```
-continued

Asp Leu Gly Pro Asp Asn Ile Arg Val Asn Ala Ile Ser Ala Gly Pro
            180             185             190

Ile Arg Thr Leu Ser Ala Lys Gly Val Gly Gly Phe Asn Thr Ile Leu
        195             200             205

Lys Glu Ile Glu Glu Arg Ala Pro Leu Lys Arg Asn Val Asp Gln Val
    210             215             220

Glu Val Gly Lys Thr Ala Ala Tyr Leu Leu Ser Asp Leu Ser Ser Gly
225             230             235             240

Val Thr Gly Glu Asn Ile His Val Asp Ser Gly Phe His Ala Ile Lys
            245             250             255

<210> SEQ ID NO 3
<211> LENGTH: 39
<212> TYPE: DNA
<213> ORGANISM: Staphylococcus aureus

<400> SEQUENCE: 3
cgcctcgaga tgttaaatct tgaaaacaaa acatatgtc                              39

<210> SEQ ID NO 4
<211> LENGTH: 33
<212> TYPE: DNA
<213> ORGANISM: Staphylococcus aureus

<400> SEQUENCE: 4
cgcggatcca atcaagtcag gttgaaatat cca                                    33
```